United States Patent
Lundborg

(10) Patent No.: US 10,206,793 B2
(45) Date of Patent: *Feb. 19, 2019

(54) SYSTEM AND METHOD FOR CONSCIOUS SENSORY FEEDBACK

(71) Applicant: OSSUR HF, Reykjavik (IS)

(72) Inventor: Goran Lundborg, Genarp (SE)

(73) Assignee: OSSUR HF, Reykjavik ( * ) Notice: Subject to any disclaimer, the term of this patent is extended or adjusted under 35 U.S.C. 154(b) by 69 days.

This patent is subject to a terminal disclaimer.

(21) Appl. No.: 15/299,808

(22) Filed: Oct. 21, 2016

(65) Prior Publication Data

US 2017/0035585 A1 Feb. 9, 2017

Related U.S. Application Data

(63) Continuation of application No. 11/886,966, filed as application No. PCT/SE2006/000367 on Mar. 23, 2006, now Pat. No. 9,480,582.

(30) Foreign Application Priority Data

Mar. 23, 2005 (SE) ...................... 0500642

(51) Int. Cl.
*A61F 2/70* (2006.01)
*A61F 2/72* (2006.01)
(Continued)

(52) U.S. Cl.
CPC ................ *A61F 2/70* (2013.01); *A61F 2/583* (2013.01); *A61F 2/68* (2013.01); *A61F 2/72* (2013.01); *A61F 2002/5061* (2013.01); *A61F 2002/6614* (2013.01); *A61F 2002/6827* (2013.01); *A61F 2002/701* (2013.01); *A61F 2002/704* (2013.01); *A61F 2002/705* (2013.01);
(Continued)

(58) Field of Classification Search
CPC .......... A61F 2/583; A61F 2/585; A61F 2/586; A61F 2002/5058; A61F 2002/5061; A61F 2002/587; A61F 2002/6827
See application file for complete search history.

(56) References Cited

U.S. PATENT DOCUMENTS 2,656,545 A 10/1953 Conzelman, Jr. et al.
3,751,733 A 8/1973 Fletcher et al.
(Continued)

FOREIGN PATENT DOCUMENTS

DE 2016295 A1 10/1971
WO 0102054 A2 1/2001

OTHER PUBLICATIONS

Anani et al., "Discrimination of Phantom Hand Sensations Elicited by Afferent Electrical Nerve Stimulation in Below-Elbow Amputees", Med Prog Technol, vol. 6, No. 3, Jun. 1979, pp. 131-135.
(Continued)

*Primary Examiner* — Adam J Eiseman
(74) *Attorney, Agent, or Firm* — Workman Nydegger

(57) ABSTRACT

A system for conscious sensory feedback for a body extremity without sensation or a body extremity prosthesis is disclosed, as well as methods for conscious sensory feedback based on said system; a glove, a sock and a body extremity prosthesis comprising said system; and use of the system.

14 Claims, 1 Drawing Sheet

(51) Int. Cl.
   A61F 2/74   (2006.01)
   A61F 2/58   (2006.01)
   A61F 2/68   (2006.01)
   A61F 2/50   (2006.01)
   A61F 2/66   (2006.01)
   A61F 2/76   (2006.01)
(52) U.S. Cl.
   CPC ... *A61F 2002/745* (2013.01); *A61F 2002/769* (2013.01); *A61F 2002/7635* (2013.01); *A61F 2002/7645* (2013.01); *A61F 2002/7655* (2013.01); *A61F 2002/7665* (2013.01)

(56) References Cited

U.S. PATENT DOCUMENTS

| | | |
|---|---|---|
| 4,770,662 A | 9/1988 | Giampapa |
| 4,808,187 A | 2/1989 | Patterson et al. |
| 5,037,376 A | 8/1991 | Richmond et al. |
| 5,246,463 A | 9/1993 | Giampapa |
| 5,413,611 A | 5/1995 | Haslam, II et al. |
| 5,888,213 A | 3/1999 | Sears et al. |
| 6,344,062 B1 | 2/2002 | Abboudi et al. |
| 6,500,210 B1 | 12/2002 | Sabolich et al. |
| 7,302,296 B1 | 11/2007 | Hoffer |
| 8,361,165 B2 | 1/2013 | Karr et al. |
| 9,480,582 B2* | 11/2016 | Lundborg ............... A61F 2/583 |
| 2004/0106881 A1 | 6/2004 | McBean et al. |
| 2006/0005845 A1 | 1/2006 | Karr et al. |
| 2008/0200994 A1 | 8/2008 | Colgate et al. |

OTHER PUBLICATIONS

Battaglia-Mayer et al., "Multiple Levels of Representation of Reaching in the Parieto-Frontal Network", Cerebral Cortex, vol. 13, No. 10, 1009-1022, Oct. 2003.
Borsook et al., "Acute Plasticity in the Human Somatosensory Cortex Following Amputation", Neuroreport, Apr. 20, 1998, vol. 9, No. 6, pp. 1013-1017.
Ceballos D et al., "Morphologic and Functional Evaluation of Peripheral Nerve Fibers Regenerated through Polyimide Sieve Electrodes Over Long-Term Implantation", J Biomed Mater Res., Jun. 15, 2002, vol. 60, No. 4, pp. 517-528.
Dhillon et al., "Residual Function in Peripheral Nerve Stumps of Amputees: Implications for Neural Control of Artificial Limbs", The Journal of Hand Surgery, Jul. 2004, vol. 29A, No. 4, pp. 605-615.
Edell et al., "A Peripheral Nerve Information Transducer for Amputees: Long-Term Multichannel Recordings from Rabbit Peripheral Nerves", IEEE Transactions on Biomedical Engineering, vol. 33, No. 2, Mar. 1986, pp. 203-214.
Gribble et al., "Overlap of Internal Models in Motor Cortex for Mechanical Loads During Reaching", Nature, vol. 417, Jun. 27, 2002, pp. 938-941.
Johansson et al., "First Spikes in Ensembles of Human Tactile Afferents Code Complex Spatial Fingertip Events", Nat Neurosci, vol. 7, Feb. 2004, pp. 170-177.
Johansson et al., "Detection of Tactile Stimuli. Thresholds of Afferent Units Related to Psychophysical Thresholds in the Human Hand", Journal of Physiology, vol. 297, 1979, pp. 405-422.
Kaas, "Topographic Maps are Fundamental to Sensory Processing", Brain Res Bull, vol. 44, No. 2, 1997, pp. 107-112.
Katz et al., "The World of Touch", Edited and Translated by Lester E. Krueger, Ohio State University, Lawrence Erlbaum Associates, Publishers,1989.
Klatzky et al., "There's More to Touch Than Meets the Eye:The Salience of Object Attributes for Haptics With and Without Vision," Journal of Experimental Psychology: General, vol. 116, No. 4, 1987, pp. 356-369.
Lundborg et al., "Tomorrow's Artificial Hand", Scand J Plast Reconstr Hand Surg, vol. 34, 2000, pp. 97-100.

Lundborg et al., "Sensory Substitution in Prosthetics", Hand Clinics, vol. 17, No. 3, Aug. 2001, pp. 481-488.
Lundborg et al., "Hearing as Substitution for Sensation: A New Principle for Artificial Sensibility," The Journal of Hand Surgery, vol. 24A, 1999, pp. 219-224.
Mann et al., "Kinesthetic Sensing for the EMG Controlled Boston Arm", IEEE Transactions on Man Machine Systems, vol. 11, No. 1, Apr. 1970, pp. 110-115.
Merzenich et al., "Reorganization of Cortical Representations of the Hand Following Alterations of Skin Inputs Induced by Nerve Injury, Skin Island Transfers, and Experience", J Hand Ther., vol. 6, No. 2, 1993, pp. 89-104.
Merzenich et al., "Variability in Hand Surface Representations in Areas 3b and 1 in Adult Owl and Squirrel Monkeys," J Comp Neurol, vol. 258, No. 2, Apr. 8, 1987, pp. 281-296.
Moran et al., "Motor Cortical Representation of Speed and Direction During Reaching", The Journal of Neurophysiology, vol. 82, No. 5, Nov. 1999, pp. 2676-2692.
Navarro et al., "Selective Fascicular Stimulation of the Rat Sciatic Nerve with Multipolar Polyimide Cuff Electrodes", Restorative Neurology and Neuroscience, vol. 18., No. 1, 2001, pp. 9-21.
Penfield et al., "Somatic Motor and Sensory Representation in the Cerebral Cortex of Man as Studied by Electrical Stimulation", Brain, vol. 60, No. 4, Jun. 4, 1937, pp. 389-443.
Picard et al., "Primary Motor Cortical Activity Related to the Weight and Texture of Grasped Objects in the Monkey", J Neurophysiol, vol. 68, No. 5, Nov. 1992, pp. 1867-1881.
Porter et al., "Corticospinal Function and Voluntary Movement", Oxford University Press, 1995.
Ramachandran, "Consciousness and Body Image: Lesson From Phantom Limbs, Capgras Syndrome and Pain Asymbolia", Philosophical Transactions of the Royal Society of London B Biological Sciences, vol. 353, 1998, pp. 1851-1859.
Ramachandran et al., "Phantoms in the Brain: Probing the Mysteries of the Human Mind", New York: William Morrow & Co Inc., 1998.
Riso, "Strategies for Providing Upper Extremity Amputees with Tactile and Hand Position Feedback—Moving Closer to the Bionic Arm", Technol Health Care, vol. 7, No. 6, 1999, pp. 401-409.
Rizzolatti et al., "The Cortical Motor System", Neuron, vol. 31, No. 6, Sep. 27, 2001, pp. 889-901.
Rodriguez et al., "Polyimide Cuff Electrodes for Peripheral Nerve Stimulation", J Neurosci Methods, vol. 98, No. 2, Jun. 1, 2000, pp. 105-118.
Rutten et al., "Neuro-Electronic Interfacing with Multielectrode Arrays", IEEE Engineering in Medicine and Biology Magazine, Jun. 1999, pp. 47-55.
Scott, "Optimal Feedback Control and the Neural Basis of Volitional Motor Control", Nat Rev Neurosci, vol. 5, Jul. 2004, pp. 532-544.
Sebelius et al., "Refined Myoelectric Control in Below-Elbow Amputees Using Artificial Neural Network and a Data Glove", The Journal of Hand Surgery, vol. 30A, Jan. 2, 2005, pp. 780-789.
Szeto et al., "Sensory Feedback Using Electrical Stimulation of the Tactile Sense", Rehabilitation Engineering, 1990, pp. 29-78.
Wallman et al., "The Geometric Design of Micro-machined Silicon Sieve Electrodes Influences Functional Nerve Regeneration", Biomaterials., vol. 22, No. 10, May 2001, pp. 1187-1193.
Weiss et al., "Rapid Functional Plasticity of the Somatosensory Cortex after Finger Amputation", EXP Brain Res., vol. 134, No. 2, Sep. 2000, pp. 199-203.
Yoshida et al., "Selective Stimulation of Peripheral Nerve Fibers using Dual Intrafascicular Electrods", IEEE Trans Biomed Eng., vol. 40, No. 5, May 1993, pp. 492-494.
European Search Report from EP Application No. 06717050.6, dated Jul. 4, 2011.
International Search Report from PCT Application No. PCT/SE2006/000367, dated Jun. 26, 2006.
Merletti et al., "Electrically Evoked Myoelectric Signals", Critical Reviews in Biomedical Engineering, vol. 19, No. 4, 1992, pp. 293-340.

(56) References Cited

OTHER PUBLICATIONS

Keenan et al., "Influence of Motor Unit Properties on the Size of the Simulated Evoked Surface EMG Potential", Exp Brain Res., vol. 169, 2006, pp. 37-49.

* cited by examiner

SYSTEM AND METHOD FOR CONSCIOUS SENSORY FEEDBACK

FIELD OF THE INVENTION

The present invention relates to a system for conscious sensory feedback for a body extremity without sensation or a body extremity prosthesis; methods for conscious sensory feedback based on said system; and a glove, a sock and a body extremity prosthesis comprising said system; and use of the system.

BACKGROUND OF THE INVENTION

The prostheses currently available on the market, e.g. arm, leg, hand, and foot prostheses, all lack conscious sensory feedback.

Congenital or traumatic amputation of e.g. a hand is a catastrophe with impact not only on occupational life and leisure activities but also on identity, social interaction and the quality of life. To compensate for the cosmetic defect various types of cosmetic hand prostheses are available, e.g. to provide a functionally useful substitution for the hand myoelectric prostheses are used, although with considerable restrictions for many patients.

Myoelectric prostheses are motorised devices which are capable of opening or closing the hand on the basis of mass EMG-signals (electromyografic signals) monitored by one surface electrode arranged on top of the extensor muscles of the amputation stump and a surface electrode arranged on top of the flexor muscles. Myoelectric hand prostheses are available on the market. Although such neurally controlled myoelectric prostheses are used by some patients there are several disadvantages in such prostheses e.g. lack of capacity for delicate movements, the prostheses usually allowing only two degrees of freedom, such as opening and closure of the hand, and lack of conscious sensory feedback. Additionally, factors like weight and limited battery lifetime are also disadvantageous in such prostheses.

Ongoing developmental research work, including the combined use of multiple EMG recording sites and artificial neural networks may soon form a base for neural control of more advanced hand prostheses, providing a large number of degrees of freedom as described by Sebelius et al. (2005). However, the lack of conscious sensory feedback still represents a fundamental major problem. The current innovation specifically addresses this problem.

The function of e.g. the human hand is based upon a complex interplay between efferent signals for motor control and afferent signals from various sensory system providing sensory feedback (Scott, 2004). The central nervous system plays a crucial role for the processing and integration of sensory input and motor output. Although the spinal cord and brain stem support "automatic functions" like limb reflexes, the motor cortex of the brain supports and controls voluntary and planned motor tasks such as reaching for an object or performing learning motor behaviour (Moran and Schwartz, 1999; Gribble and Scott, 2002). Although the planning of motor activities involves several cortical regions such as the frontal parietal region-premotor cortex (Rizzolatti and Luppino, 2001; Battaglia-Mayer et al., 2003) the execution of goal-directed and skill motor tasks is based on neural activity in the primary motor cortex M1 (Porter and Lemon, 1993). The activity of M1 is to a great extent modulated and influenced by sensory feedback from several senses such as touch, vision, hearing and proprioception. Many nerve cells in M1 respond strongly to cutaneous stimulation of the hand (Picard and Smith, 1992), a fact which strongly reflects how grip functions of the hand are dependent on skin contact and cutaneous stimulation constituting a sensory feedback (Scott, 2004).

The sense of touch is essential for making a hand "belonging to the body". A hand without sensory functions is perceived as a foreign body and may even be denied by the owner (Ramachandran and Blakeslee, 1998). In addition, regulation of grip force and execution of delicate motor tasks in the hand are dependent on a sensory input from the hand to the central nervous system. Typically, the sensibility of the glabrous skin of the hand is based on four types of mechanoreceptors, localised in subepidermal and subcutaneous areas, and responding to static pressure or vibrotactile stimuli (Johansson and Vallbo, 1979; Johansson and Birznieks, 2004). Among receptors responding to vibration are Meissner's corpuscles, located in the subepidermal papillae, with small receptive fields (Fast Adapting—type I-FA I receptors) and Pacini's corpuscles, located in subcutaneous layers possessing large receptive fields (Fast Adapting type II—FA II receptors-). The Merkel cells, located just beneath the epithelium, respond to static measure and have small receptive fields (Slowly Adapting—type I-SA I receptors). Ruffini's organ, located subcutaneously, responds mainly to stretching (SA II receptor). The extremely well developed tactile functions of the hand make the hand a sensing organ. The sense of touch is essential for exploring the surrounding world. In active touch we can, without using vision, recognise and identify textures, shapes and forms of small items (Klatsky et at, 1987; Katz, 1989). The well developed sensory function of the hand is reflected in the representational area of the hand in somatosensory cortex, occupying a very substantial part (Merzenich and Jenkins, 1993; Kaas, 1997).

Various principles for providing sensory feedback in hand prostheses have been tried over the years (see reviews by (Riso, 1999; Lundborg and Rosen, 2001). Three different approaches have been used:

1) sensory substitution (use of an intact sensory system to replace the missing one);
2) direct stimulation of intact nerves;
3) transferred cutaneous sensation implying stimulation of intact skin in a remote area of the body.

Sensory substitution, using an intact sensory system, is automatically used by amputees using myoelectric prostheses, which utilise vision to guide the movements of the prosthetic hand. The use of hearing as substitution for missing sensation has been described as an effective strategy in major nerve injuries leaving the hand devoid of sensation and has also been tried in hand prostheses as described in WO9848740 (A1) by Lundborg. According to this principle electrical signals, elicited by vibrotactile stimuli and recorded by miniature microphones at fingertip level when fingers are touched, are fed to a stereo processor which transfers weighted signals to earphones applied to the left and right ears, making possible spatial resolution of the hand. In this way the "friction sound" associated with active touch of various textures can be recognised and easily associated with touch of specific textures (Lundborg et al., 1999).

It has been demonstrated that sensations can be evoked when sensory nerves of the residual limb are electrically stimulated (Anani and Korner, 1979). Some topographic discrimination can be achieved by selective stimulation of different fascicles using percutaneous stimulatory electrodes (Anani and Korner, 1979). However, the spatial resolution for fibre activation is low using this technique and the quality of perceptived sensation is low.

To improve the principle of direct nerve stimulation various techniques for micro stimulation of tactile afferents have been proposed. More natural sensations can be evoked when individual cutaneous afferent fibres are electrically activated in isolation (Riso, 1999). To further refine the contact nerve tissues, stimulatory devices of various types of nerve interfaces have been used in laboratory environment (Riso, 1999). Some of these techniques require growth of regenerating axons into a stimulation device. For instance, using "sieve electrodes"—regenerating axons from a transected nerve is directed to penetrate the matrix of pores to make appropriate electrode contacts (Wallman et al., 2001; Ceballos et al., 2002). With this principle groups of axons can penetrate separate perforations in the chip and the electrode contact can address either individual pores or separate sections of the transversely positioned sieve electrode. Although the foreign body reaction induced by silicone sieve electrodes is discrete and the long term effects of such electrode implantation are not known. Selective fascicular stimulation can also be achieved by the use of multipolar cuff electrodes (Rodriguez et al., 2000; Navarro et. al., 2001). Another concept for a type of nerve regeneration interface is to introduce, co-axially, platinum-iridium wires or analogous devices into the lumen of a regeneration tube (Edell, 1986; Riso, 1999). Another technique is to use a "brush array" of micromachined needle electrodes inserted into a peripheral nerve (Rutten et al., 1999). Peripheral nerves can also be interfaced by introducing longitudinal fine wires into the nerve trunk (Dhillon et al., 2004) or into separate nerve fascicles (Yoshida and Horch, 1993). The theoretical advantage of the nerve-interface strategies discussed above is that sensory stimuli can be directly transferred into peripheral nerves and can thereby reach CNS. However, there are several drawbacks and difficulties. A transcutaneous passage device or telemetric techniques are required to transfer the sensory information from the outside of the body to the inside. The electric stimulation of sensory fascicles may not be modality-specific and may give rise to unphysiological and weird sensory perception. The nerve interface principle, based on implanted electronic devices will therefore remain on the experimental stage for many years to come.

Attempts to use transferred cutaneous stimulation to remote skin areas were already tried several decades ago. According to this principle remote skin areas of the body can be subjected to electro-cutaneous stimulation (Szeto and Riso, 1990) or vibration (Mann and Reimers, 1970). Although such types of stimuli, when proportional to the pressure which is applied to sensors in the prostheses, can serve as a feedback system for regulation of the grip force in a myoelectric prostheses (Lundborg et al., 1999) they give rise to very unpleasant and non-physiological sensations. In addition, stimulation of remote skin areas is not easy to correlate with stimulation of the hand since the cortical representations of the respective body parts are widely apart and can therefore not serve as a useful system for conscious sensory feedback. No attempts have been made to correlate stimulation of topographically specific skin areas to stimuli applied to analogous topographically defined components of a hand prosthesis.

Amputation of a hand has immediate and long-lasting effects on the functional organisation of brain cortex (Merzenich and Jenkins, 1993; Weiss et al., 2000). Normally the cortical "body map" constitutes representational areas of all body parts which are represented in somatosensory cortex in a specific topographical order and in sizes which are proportional to their sensory competence (Kaas, 1997). Thus, the hand and the face, presenting exceptionally well developed sensory functions, occupy a major part of the somatosensory cortex. According to the cortical body map the face representational area is localised immediately caudal to the hand representation, and the representational area of the forearm is localised immediately cranial to the hand representational area (Penfield and Boldrey, 1937; Merzenich et at, 1987; Kaas, 1997). If a hand is amputated there suddenly is a "silent" cortical area, previously devoted to the hand. This is followed by a rapid expansion of the face and forearm representational areas to include the former hand representational area. It has been shown that this phenomenon may already occur within 24 hours after amputation (Borsook et al., 1998). Touch of the forearm or the face then results in sensory phenomena in the phantom limb as a result of cortical expansion of the forearm representation. Thus, a "phantom hand" can sometimes usually be mapped in the distal part of the residual forearm of the amputee (Ramachandran, 1998). Such cortical functional reorganisation phenomena—an expression for "brain plasticity"—occur rapidly and may remain permanently.

The same problem with lack of conscious sensory feedback also applies to body parts lacking sensation or having impaired sensation, e.g. diabetes patients.

SUMMARY OF THE INVENTION

The object of the present invention is to solve the abovementioned problems with lack of conscious sensory feedback in prostheses and body parts lacking sensation.

This object is achieved by a system for conscious sensory feedback of a body extremity without sensation or a lacking body extremity, comprising at least one sensor (2) to be arranged on said body extremity without sensation or to be arranged on a body extremity prosthesis; a tactile display (5) comprising at least one signal transducer (4), wherein each signal transducer is to be arranged on the skin of an intact neighbouring body extremity of a patient; wherein said at least one sensor (2) when subjected to at least one stimuli has the ability to transfer a signal to said at least one signal transducer (4) which has the ability to transduce said signal to said stimuli on naturally occurring nervous components in the skin of the neighbouring intact body extremity; wherein said system is attachable to and detachable from the patient without surgical intervention.

The object according to the present invention may also be achieved by a glove or a sock comprising the system as described above. The glove may be used on a hand, arm or finger without sensation or partially without sensation; and the sock may be used on a foot, leg or toe without sensation or partially without sensation.

The object according to the present invention may also be achieved by a method for conscious sensory feedback for a body extremity without sensation or a lacking body extremity of a patient by using a system according to the present invention, wherein it comprises the following steps:

a) applying said at least one sensor to the body extremity without sensation or a body extremity prosthesis at one or more locations where conscious sensory feedback is desired, b) identifying, optionally before step a), one or more locations on the skin of an intact neighbouring body extremity at which location the nerve components in the skin represent the previously existing or defect nervous components at said one or more locations where conscious sensory feedback is desired, c) applying a tactile display comprising at least one signal transducer on the skin of the intact neighbouring body extremity at one or more locations identified under step b), wherein when said at least one sensor of the patient is subjected to at least one stimuli, the patient perceives said at least one stimuli on the body extremity prosthesis.

Additionally, the object according to the present invention may also be achieved by a method for conscious sensory feedback for a body extremity without sensation or a lacking body extremity of a patient by using a system according to the present invention, wherein it comprises the following steps:

a) applying said at least one sensor to the body extremity without sensation or a body extremity prosthesis at one or more locations where conscious sensory feedback is desired, b) optionally identifying, optionally before step a), one or more locations on the skin of an intact neighbouring body extremity at which location the nerve components in the skin represent the previously existing or defect nervous components at said one or more locations where conscious sensory feedback is desired, c) applying at least one signal transducer of a tactile display to the skin of an intact neighbouring body extremity at one or more locations, d) repeatedly subjecting said at least one sensor to at least one stimuli during visual observation or hearing by the patient until the patient has learned to recognize said at least one stimuli and to correlate it to said location(s) on said intact neighbouring body extremity, wherein when said at least one sensor of the patient is subjected to at least one stimuli, the patient perceives said at least one stimuli on the body extremity prosthesis or the body extremity without sensation.

The object according to the present invention may also be achieved by a body extremity prosthesis fully or partially comprising the system according to the present invention.

BRIEF DESCRIPTION OF THE DRAWINGS

Different embodiments of the present invention will now be described, by way of example, with reference to the accompanying schematic drawings, in which.

DETAILED DESCRIPTION OF PREFERRED EMBODIMENTS

Figures 1, 2:
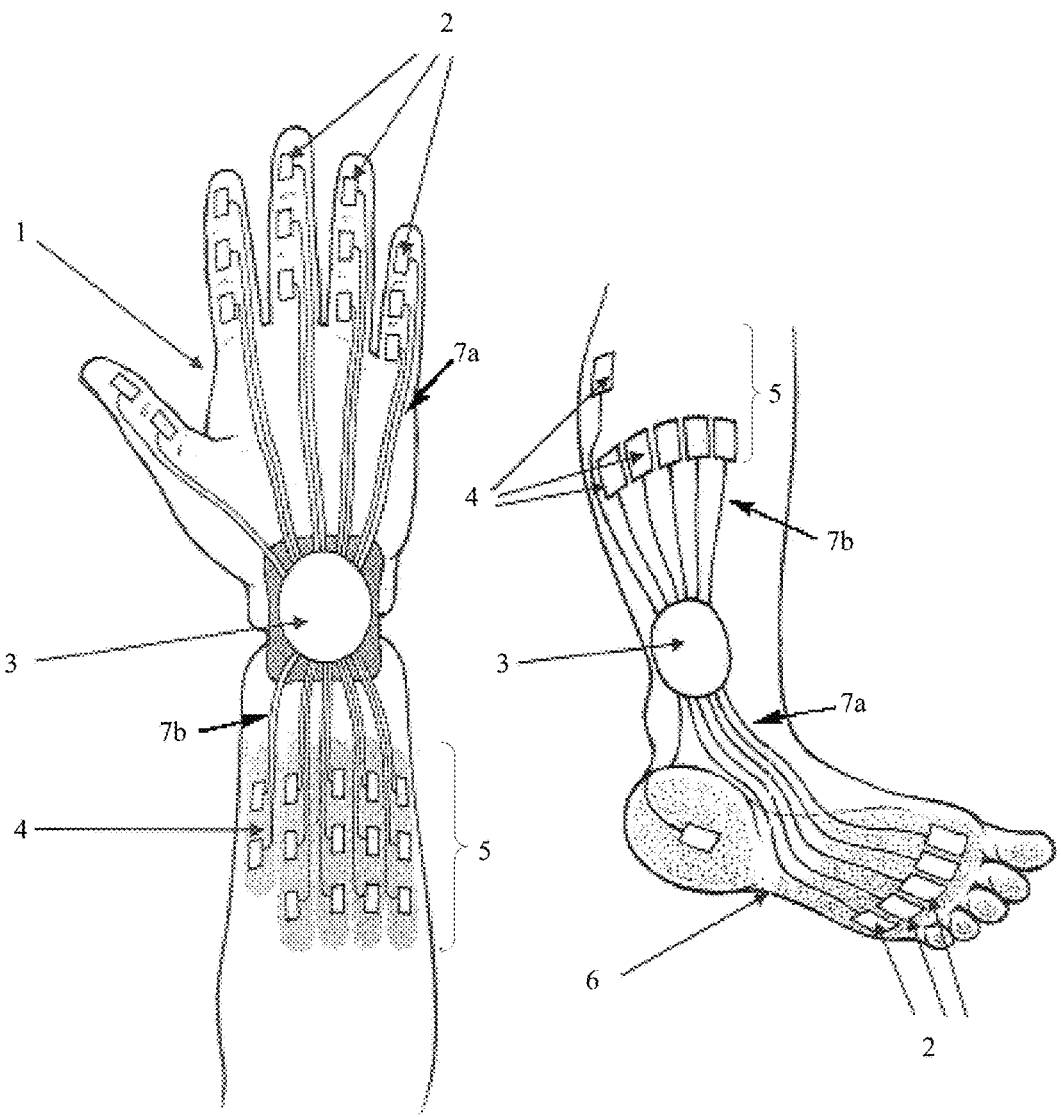
FIG. 1 is a schematic representation of a hand and arm provided with the system according to the present invention.
FIG. 2 is a schematic representation of a foot and lower leg provided with the system according to the present invention.

To reconstruct all delicate sensory functions of e.g. a human hand in an artificial hand is an impossible task. Such a system would require several types of sensors in the artificial hand for registration of e.g. pressure, vibration, shear forces, temperature, moisture and pain (Lundborg, 2000; Lundborg and Rosen, 2001). It also requires a system for feeding the central nervous system (CNS) with sensory input. An efficient system should offer a conscious sensibility—not only a local reflex loop system in the hand, so called slip sensors—never reaching CNS, and it should offer a spatial resolution of the hand to make possible perception of tactile stimuli applied to different areas of the hand.

The present invention is based on current insights into brain plasticity mechanisms, implying that e.g. a pre-amputation hand representation in brain cortex becomes occupied by cortical expanding adjacent representations including that of the forearm, and that tactile stimuli applied to the forearm of such an amputee therefore may be perceived as stimuli applied to the "phantom" hand or to an attached hand prosthesis, as well as to a foot or a leg. According to this principle physical or electrical signals, exerted by touch stimuli, vibrotactile or temperature stimuli applied to hand prostheses can be transferred to a tactile display, comprising signal transducers, applied to the skin of the forearm or lower leg (calf), can be perceived as true sensory stimuli applied to a body extremity prosthesis, e.g. a hand prosthesis or a forearm prosthesis; or to a body extremity without sensation. By mapping individual parts of the hand in a topographical "mirror fashion" on the forearm skin the system allows for a three-dimensional topographical resolution of touch stimuli, vibrotactile stimuli and other types of sensory stimuli applied to the hand prosthesis. A person skilled in the art will also appreciate that the system may be applied also to other extremities, such as hands without sensation as well as foot prostheses and feet without sensation, or where the body extremity partly is lacking sensation.

The term "without sensation" used in the present application is intended to mean a body extremity which has reduced sensation, or no sensation and/or a part of a body extremity lacking or having reduced sensation. Body extremities may lack sensation, e.g. due to nerve injury or metabolic neuropathy. In such situations the body extremity is very vulnerable to injury since sensory feedback is lacking.

The term "body extremity" used herein is intended to mean an arm or a leg or a part thereof, e.g. one or more fingers or toes or parts thereof, a whole hand or foot or a part thereof, the forearm or lower leg, such as the calf, or a part thereof and the upper arm or the thigh or a part thereof.

The terms "body extremity prostheses" or "prostheses" used herein are intended to mean an artificial replacement of a body extremity as defined above and comprise conventional prostheses used as replacements for arms and legs and any parts thereof. In one embodiment said body extremity prostheses may have the whole system according to the present invention included.

The term "neighbouring intact body extremity" used herein is intended to mean the intact part of the extremity or the part of extremity which is closest or close to a body extremity without sensation or to a body extremity prosthesis as defined above. Said intact part is sometimes also called a "stump". E.g., if a hand lacks sensation or is completely lacking, e.g. due to amputation, the neighbouring intact body extremity is the lower part of the forearm.

The term "intact" used herein is intended to mean that the residual extremity in question has undamaged or substantially or partly undamaged tissue.

The expression "previously existing or defect nervous components" used herein is intended to mean nervous components which were present in a body extremity which thereafter has been lost of any reason, or nervous components which of any reason is fully or partly inactive in a body extremity without sensation.

The term "attachable and detachable" used herein is intended to mean that it is possible to apply the system according to the present invention to the patient, without surgical intervention, when desired and also to remove it from the patient when desired, preferably in an easy and simple way for the patient or an assisting person. This means that no parts of the system are permanently secured to any part of the patient's body. However, parts of the system may be permanently secured to, or included in, a body extremity prosthesis as defined above, but not necessarily.

The term "glove" used herein is intended to mean any glove-like or tubular substantially elastic material covering at least a body extremity without sensation or a body extremity prosthesis as defined above. Said glove may be made of any conventional suitable material which is comfortable for the patient, and the system according to the present invention or parts thereof may be embedded in said glove in such a way that said at least one sensor and, optionally, the signal transducers of said tactile display is brought into adequate contact with the body extremity without sensation, the body extremity prosthesis or the skin of the neighbouring intact body extremity.

The term "sock" used herein is intended to mean any sock-like or tubular substantially elastic material covering at least a body extremity without sensation or a body extremity protheses as defined above. Said sock may be made of any conventional suitable material which is comfortable for the patient, and the system according to the present invention or parts thereof may be embedded in said sock in such a way that said at least one sensor and, optionally, the signal transducers of said tactile display is brought into adequate contact with the body extremity without sensation, the body extremity prosthesis or the skin of the neighbouring intact body extremity.

Impaired or absence of sensation is commonly seen in severe metabolic neuropathy, e.g. diabetes. In such cases the plantar part of the foot is especially vulnerable to injury since sensory feedback is lacking, although sensation of the calf may be preserved. The present invention for sensory feedback is therefore useful for application in such cases.

Amputation of the foot is seen primarily in cases of severe neuropathy such as diabetes, but also as a result of traumatic injury. The present invention for sensory feedback is designed to be applicable also in such cases.

As stated above the present invention provides a system for conscious sensory feedback for e.g. a hand prosthesis, a hand without sensation, a foot prosthesis or a foot without sensation, which system provides conscious sensibility including tactile discriminative functions, with sensation to pressure and with capacity for spatial resolution. The present invention utilises transferred cutaneous sensibility, e.g. from the artificial hand to the forearm, using a system which is capable of mentally perceived natural sensation in the artificial hand via a tactile display, including at least one signal transducer, stimulating the skin of a neighbouring intact body extremity, e.g. the forearm, or the upper arm if the forearm is missing. According to the present invention naturally occurring nervous components in the skin such as mechanoreceptors may be utilised. The tactile display should be applied to the body part having a cortical representation in the brain, preferably arranged as close as possible to the cortical representational area of the amputated body part, i.e. as far distally as possible in the residual limb. The signal transducers of the tactile display should induce a stimulus mimicking the natural stimulus as much as possible, e.g. pressure to an artificial hand should induce the same type of pressure to the stimulated skin and vibrotactile stimuli should induce vibrotactile stimuli to the recipient skin. Preferably the signal transducers are arranged on a support and may be adapted to individual patients of for best performance. In the present invention "adapted" means not permanently arranged, i.e. it is possible to rearrange said signal transducers.

FIG. 1. illustrates one embodiment of the system, wherein sensors (2) are applied to a hand prosthesis or a hand without sensation or a glove (1) and are connected to a processor (3) via electrical or hydraulic conduits (7a), said processor (3) being connected by electrical or hydraulic conduits (7b) to signal transducers (4), arranged on the forearm, forming a tactile display (5).

FIG. 2. illustrates one embodiment of the system, wherein sensors (2) are applied to a foot prosthesis or a foot without sensation or a sock (6), connected to a processor (3) via electrical or hydraulic conduits (7a), said processor (3) being connected by electrical or hydraulic conduits (7b) to signal transducers (4), arranged on the calf, forming a tactile display (5).

The sensor (2) to be used according to the present invention may be a pressure sensor, a vibrotactile sensor, a temperature sensor, a tension sensor, or any combination thereof, or any other sensor capable of responding to a stimuli, and may be one sensor or a plurality of sensors, e.g. piezo-resistive sensors such as Interlinks Force Sensing Resistor type 149NF available from Interlink Electronics, Camarillo, USA; small electric condenser microphones such as EM-6LS available from Gocco Trading Co. Tokyo, Japan. Multisensors having the ability to sense different stimuli at the same time are also applicable. Each sensor (2) can be secured on the desired location, e.g. a finger, in any convenient way, e.g. using circular strap, tape, glue, bur fastener, as well as being self-adhesive. The sensors (2) of the system according to the present invention are to be placed on the sites of the body extremity without sensation or the body extremity prosthesis at which the conscious sensory feedback is desired. The amount of sensors (2), the type of sensors (2) and the spatial arrangement of the sensors depend on the type and intensity of the sensory feedback desired, the anatomy of the individual patient and the size of the sensors (2). In one embodiment each sensor (2) is connected via an electrical conduit (7a), optionally via a processor (3), to the corresponding signal transducers (4) in the tactile display (5). The type of electrical conduit (7a, 7b) is not critical, and electrical conducts conventionally used are applicable here. Additionally, the sensors (2) may be in connection with said signal transducer (4) by wireless connection, e.g. infrared connections or other wireless connections known to a person skilled in the art. Furthermore, the connection may be of hydraulic type, e.g. tubes filled with a fluid. Furthermore, one sensor (2) may be in contact with or connected to, as mentioned above, one or more signal transducers (4) and consequently one signal transducer (4) may be in contact with or connected to, as mentioned above, one or more sensors (2).

In one embodiment the system comprises a processor (3), which collects a signal from the sensor (2) and processes and/or converts the signal to a desired output signal, which is transferred to said tactile display (5). The processor is preferably a pneumatic, electromechanical or electric device.

According to the present invention the tactile display (5), which includes the signal transducers, and optionally also the processor, may be arranged in the casing of the body extremity prosthesis, or in a flexible support to be applied to a casing of a body extremity prosthesis or directly to a body extremity without sensation.

The tactile display (5) comprises said at least one signal transducer (4) and, optionally, a support carrying said at least one signal transducer (4). This is not restricted to any particular form or any particular material. According to the present invention a "support" means a material, preferably flexible, which may be used to spatially arrange the signal transducers and maintaining said transducers on the desired body extremity part. When the tactile display (5) comprises a support it may have the form of an elastic casing, a sleeve, a cuff, a dressing, a bur fastener or any other conventionally formed material which is easy to attach to and detach from the neighbouring body extremity or a body extremity prosthesis. Furthermore, said support may be included in a body extremity prosthesis e.g. applied to the inner surface of a casing. The main purpose of the support when present is to keep the signal transducers in the correct spatial positions when attached to the intact neighbouring body extremity, whereby optimal signal transduction to the naturally occurring nervous components in the skin of said neighbouring body extremity takes place. The exact positions of these naturally occurring nervous components to be stimulated is of course individual for each patient, but often they are located in approximately predefined areas of the skin and may be located by a person skilled in the art having this knowledge and, optionally, utilizing some trial-and-error tests. Conveniently, these positions are located on the skin in advance and then each signal transducer to be placed on each corresponding position on the skin is arranged on said support in such a way that each signal transducer contacts the corresponding position on the skin each time the tactile display of the system is attached on the intact neighbouring body extremity. Each single transducer may be secured to the support in any convenient way, e.g. by circular strap, tape, glue, bur fastener, as well as being self-adhesive, as long as each signal transducer is able to be brought in adequate contact with the corresponding position on the skin. However, if the naturally occurring nervous components are difficult to locate for some reason it is also possible according to the present invention to apply the system to a body extremity without sensation or a body extremity prosthesis and for the patient to learn how to discriminate between different stimuli, although the signal transducers are not placed in the optimal arrangement. This may for example be done with the help of hearing or vision, wherein e.g. a finger of a hand, provided with the system according to the invention, is exposed to a stimuli such as heat, and the heat is then registered by one or more sensors and the heat stimuli is transferred to a neighbouring intact body extremity as described above. The patient will, by observing which finger that is exposed to the stimuli, register the type of stimuli and where it is applied on the intact neighbouring body extremity and learn to recognize such a stimuli and correlate it to the correct location. By repeating such a procedure a patient can learn to discriminate between different stimuli and the location of the stimuli. This naturally applies to all possible embodiments according to the present invention.

In one embodiment the support may not be needed in the tactile display. In such a case, the tactile display comprises a bunch of electrical conduits, hydraulic conduits or wireless connections to which signal transducers are connected. Each time the system according to the present invention is to be used, each signal transducer has to be applied to the corresponding position on the skin, which may be permanently marked in advance with a view to facilitating the measure to find the correct positions on the skin between each use of the system and the next.

According to one embodiment of the present invention the system for conscious sensory feedback may be removed without the need for surgical intervention or, in the most cases, without any assistance, e.g. it may be included in a prosthesis known in the art. In the case of a body extremity without sensation the components of the systems may be arranged on the body extremity by bur fasteners.

More precisely, to achieve the spatial resolution required of e.g. an artificial hand individual fingers of the artificial hand are projected into a "hand map"—a mirror picture of the artificial hand—where individual and well separated areas in the skin area are stimulated by signal transducers of the tactile display. The tactile display is situated as close as possible to the artificial body extremity, e.g. inside the casing of a prosthesis. Thus, the arrangement of the signal transducers on the tactile display should represent a "mapping" of the body extremity, e.g. a hand, applied onto the skin with correct orientation of the map as related to the body extremity anatomy. In the case of a hand separate maps may be applied to the volar and dorsal parts of the distal forearm or more proximally in the residual limb (see FIG. 1). The same system may be applied also to a foot prosthesis or a foot without sensation (see FIG. 2).

In one embodiment according to the present invention pressure sensors are positioned in an artificial hand, i.e. a hand prosthesis, primarily at the levels of the thumb pulp and finger pulps, and sensors may be placed also on the volar aspects of the middle and proximal phalanges and on various parts of the hand vola. As stated above the pressure sensors may be of electro-conductive type (e.g. electro active polymers, piezo-resistive elements, capacitive sensors) or analogous types. Sensors detecting both static and dynamic pressure can be of optical, magnetical, mechanical or pneumatic type. A tactile display for pressure is positioned on the volar or dorsal aspect of the forearm with separate displays, i.e. signal transducers, for individual fingers, parts of fingers and, if applicable, separate segments of the volar part of the hand. The tactile display, comprising the signal transducers, may be included in the casing of the artificial hand around the forearm or be applied directly to the intact body extremity, without being a part of the casing, and should be as large as possible to compensate for the more "diluted" distribution of mechanoreceptors in the forearm as compared to the normal hand. The signal transducers of the tactile display should induce natural pressure to the skin in any of several possible ways e.g. a pneumatic system with expanding mini-cuffs, synchronised with pressure receptors in the hand, constituting a "communicating vessel" system, e.g. vibrotactile activators such as vibrating motors available from Alcom (originally designed for use in mobile phones), miniature loudspeakers and servo-motors available from Graupner, micromuscles or analogous devices, voice coils, micromuscles or analogous devices. A person skilled in the art may easily implement a similar system to be used on a body extremity without sensation, such as a foot, and additionally to a prosthesis for use on a body extremity.

According to one embodiment of the present invention sensors for vibrotactile perception are arranged in the artificial hand in the same topographical order as mentioned above. Piezoelectric devices or capacitive sensors or analogous devices may be used, and may be incorporated in the substance of the artificial hand or applied to the dorsal or volar aspects of the fingers. The vibrotactile display is based on individual devices such as electroactive polymers, piezoelectric elements or other types of vibrating elements, for instance DC motors or membranes according to the same principle as being used in loudspeakers, e.g. vibrating motors, miniature loudspeakers, voice coils or Peltier elements, for registration of temperature. The system can be complemented with the use of hearing, as described by Lundborg et al., 1999. As with the signal transducers for touch/pressure also individual vibrotactile signal transducers for separate fingers or parts of the hand should preferably be spatially arranged, enlarged and separated as much as possible to give optimal spatial resolution, and the same tactile display may comprise signal transducers for touch/pressure as well as vibro-cutaneous perception.

In one embodiment according to the present invention sensors for detecting angular movements, magnetic sensors, gyroscopes or analogous devices are used. Microelectric mechanical systems (MEMS) may be used to measure acceleration, and stretching forces may be recorded by e.g. gauge meters.

The system according to the present invention may also be used for spatial localisation of different fingers in an body extremity prosthesis as well as for graded sensory feedback to regulate the grip force in a denervated body extremity, i.e. a body extremity without sensation or a body extremity prosthesis.

The principles of the invention are further illustrated in the following non-limiting examples.

EXAMPLES

Example 1

In an amputee, using a myo-electric prosthesis, piezo-resistive membranes as sensors, available from Interlink Electronics, Camarillo, USA, were fixed to the volar part of the fingers of the prosthesis by the use of circular tape. Electric signals, induced by pressure, were processed by a processor and transposed to a tactile display comprising vibrating motors as signal transducers, placed parallel but clearly separated, on the volar aspect of the forearm in a transverse fashion from the medial to the lateral side. The vibrating motors were fixed by a circular strap around the forearm. Touch applied to one or several fingers of the prosthesis induced a vibro-tactile stimulus to the skin of the forearm, and the patient easily learned to discriminate, without using vision, between the individual fingers of the prosthesis.

Example 2

In an example analogous to Example 1 a patient without sensation in the hand, due to nerve injuries at the wrist level, is treated. Analogous to example 1 electrical signals from individual fingers were processed by a processor and transposed to the vibrating motors, arranged parallel in a tactile display as described above. Also this patient could easily, without using vision, discriminate in a correct way between various pressure levels applied to individual fingers.

Example 3

Miniature servo-motors as signal transducer, available from Graupner, Pico-XC50, were placed in analogy with what is described above for Example 1. A lever was placed on the shaft of the servo-motors so that a pushing force could be applied to the user's skin in proportion to the pressure force which was applied to the prosthesis fingers, but use could also be made of the sensory feedback to control the grip force of the hand.

Example 4

Vibrating motors were placed on the dorsal part of the calf of a foot lacking sensation in positions as indicated in FIG. 2. Piezo-resisting membranes were arranged in positions indicated in FIG. 2. Pressure to anyone of the piezo-electric membranes in various positions on the sole of the foot could be spatially discriminated by the patient on the basis of the vibro-tactile stimulation of corresponding skin areas in the calf.

Example 5

In analogy with Example 4 a foot with impaired sensation gave the same result.

REFERENCES

Anani A, Komer L. (1979). Discrimination of phantom hand sensations elicited by afferent electrical nerve stimulation in below-elbow amputees. Med Prog Technol 6:131-135.
Battaglia-Mayer A, Caminiti R, Lacquaniti F, Zago M. (2003). Multiple levels of representation of reaching in the parieto-frontal network. Cereb Cortex 13:1009-1022.
Borsook D, Becerra L, Fishman S, Edwards A, Jennings C, Stojanovic M, Papinicolas L, Ramachandran V, Gonzalez R, Breiter H. (1998). Acute plasticity in the human somatosensory cortex following amputation. Neuro Report 9:1013-1017.
Ceballos D, Valero-Cabre A, Valderrama E, Schuttler M, Stieglitz T, Navarro X. (2002). Morphologic and functional evaluation of peripheral nerve fibers regenerated through polyimide sieve electrodes over long-term implantation. J Biomed Mater Res 60:517-528.
Dhillon G S, Lawrence S M, Hutchinson D T, Horch K W. (2004). Residual function in peripheral nerve stumps of amputees: implications for neural control of artificial limbs. J Hand Surg [Am] 29:605-615; discussion 616-608.
Edell D J. (1986). A peripheral nerve information transducer for amputees: long-term multichannel recordings from rabbit peripheral nerves. IEEE Trans Biomed Eng 33: 203-214.
Gribble P L, Scott S H. (2002). Overlap of internal models in motor cortex for mechanical loads during reaching. Nature 417:938-941.
Johansson R S, Birznieks 1. (2004). First spikes in ensembles of human tactile afferents code complex spatial fingertip events. Nat Neurosci 7:170-177.
Johansson R S, Vallbo A B. (1979). Detection of tactile stimuli. Thresholds of afferent units related to psychophysical thresholds in the human hand. J Physiol 297: 405-422.
Kaas J R. (1997). Topographic maps are fundamental to sensory processing. Brain Res 3044:107-112.
Katz D. 1989. The world of touch. London: Lawrence Erlbaum Associates.
Klatsky R L, Lederman S, Reed C. (1987). There's more to touch than meets the eye: The salience of object attributes for haptics with and without vision. J Exp Psych General 116:356-369.
Lundborg G. (2000). Tomorrow's artificial hand. Scand J Plast Reconstr Surg Hand Surg 34:97-100.
Lundborg G, Rosen B. (2001). Sensory substitution in prosthetics. Hand Clin 17:481-488, ix-x.
Lundborg G, Rosen B, Lindberg S. (1999). Hearing as substitution for sensation—a new principle for artificial sensibility. J Hand Surg 24A:219-224.
Mann R W, Reimers S D. (1970). Kinesthetic sensing for the EMG controlled "Boston Arm". IEEE Trans Man Mach Syst 11:110.

Merzenich M M, Jenkins W M. (1993). Reorganization of cortical representations of the hand following alterations of skin inputs induced by nerve injury, skin island transfers, and experience. J Hand Ther 6:89-104.

Merzenich M M, Nelson R J, Kaas J Hea. (1987). Variability in hand surfacerepresentations in areas 3 band 1 in adult own and squirrel monkeys. J Comp Neurol 258:281-297.

Moran D W, Schwartz A B. (1999). Motor cortical representation of speed and direction during reaching. J Neurophysiol 82:2676-2692.

Navarro X, Valderrama E, Stieglitz T, Schuttler M. (2001). Selective fascicular stimulation of the rat sciatic nerve with multipolar polyimide cuff electrodes. Restor Neurol Neurosci 18:9-21.

Penfield W, Boldrey E. (1937). Somatic motor and sensory representations in the cerebral cortex of man as studied by elecreical stimulation. Brain 60:389-443.

Picard N, Smith A M. (1992). Primary motor cortical activity related to the weight and texture of grasped objects in the monkey. J Neurophysiol 68: 1867-1881.

Porter R, Lemon R N. 1993. Cortical function and voluntary movement. Oxford:Clarenton.

Ramachandran V. (1998). Consciousness and body image: lesson from phantom limbs, Capgras syndrome and pain asymbolia. Philosophical Transactions of the Royal Society of London B; Biological Sciences 353:1851-1859.

Ramachandran V, Blakeslee S. 1998. Phantoms in the brain. New York: William Morrow & Co Inc.

Riso R. (1999). Strategies for providing upper extremity amputees with tactile and hand position feedback—moving closer to the bionic arm. Technol Health Care 7:401-409.

Rizzolatti G, Luppino G. (2001). The cortical motor system. Neuron 31:889-901.

Rodriguez F J, Ceballos D, Schuttler M, Valero A, Valderrama E, Stieglitz T, Navarro X. (2000). Polyimide cuff electrodes for peripheral nerve stimulation. J Neurosci Methods 98:105-118.

Rutten W L, Smit J P, Frieswijk T A, Bielen J A, Brouwer A L, Buitenweg J R, Heida C. (1999). Neuro-electronic interfacing with multielectrode arrays. IEEE Eng Med BioI Mag 18:47-55.

Scott S H. (2004). Optimal feedback control and the neural basis of volitional motor control. Nat Rev Neurosci 5:532-544.

Sebelius F. Rosen B. Lundborg G (2005): Refined myoelectric control in below-elbow amputees using artificial neural network and a data glove, J. Hand. Surg. 30A; 780-789.

Szeto A Y, Riso R. 1990. Sensory feedback using electrical stimulation of the tactile sense. In: Smith R V, Leslie J H, editors. Rehabilitation Engineering. Boca Raton:CRC. p 29-78.

Wallman L, Zhang Y, Laurell T, Danielsen N. (2001). The geometric design of micromachined silicon sieve electrodes influences functional nerve regeneration. Biomaterials 22:1187-1193.

Weiss T, Miltner W, Huonker R, Friedel R, Schmidt I, Taub E. (2000). Rapid functional plasticity of the somatosensory cortex after finger amputation. Exp Brain Res 134: 199-203.

Yoshida K, Horch K. (1993). Selective stimulation of peripheral nerve fibers using dual intrafascicular electrodes. IEEE Trans Biomed Eng 40:492-494.

The invention claimed is:

1. A system that provides conscious sensory feedback to a patient, the system comprising:

first and second sensors configured in a spatial pattern and adapted to be arranged on a region where conscious sensory feedback is desired, the first and second sensors connecting to first and second sensor conduits, respectively;

a processor arranged to receive at least one signal from the first and second sensors via the first and second sensor conduits, respectively;

a tactile display connected to the processor, the tactile display arranged to be placed in an area of the patient neighboring the region where conscious sensory feedback is desired, the tactile display comprising:

first and second transducer conduits connecting to the processor, and corresponding to the first and second sensor conduits for receiving output by the processor, respectively;

first and second transducers arranged for cooperating with receptive fields on the area of the patient, and connecting to the first and second transducer conduits, respectively, each of the first and second sensors being topographically correlated with a respective one of the first and second transducers; and a support adapted to hold and position the first and second transducers proximate to the receptive fields to map spatial recognition and association of the region where conscious sensory feedback is desired by mapping signals from the first and second sensors by the first and second transducers, respectively, when a stimulus is applied to the region.

2. The system of claim 1, wherein the spatial pattern forms a mirror image map of the spatial pattern of the first and second sensors.

3. The system according to claim 1, further comprising a body extremity prosthesis in which the first and second sensors are positioned.

4. The system according to claim 1, wherein the first and second sensors are selected from the group consisting of a pressure sensor, a vibrotactile sensor, a temperature sensor, a piezo-resistive sensor, a microelectric mechanic system (MEMS), a gauge meter, a gyroscope, a magnetic sensor, an electric condenser microphone, and a tension sensor.

5. The system according to claim 1, said processor being arranged to process first and second signals received from the first and second sensors and transfer said first and second signals to the first and second transducers, respectively.

6. The system according to claim 1, wherein the processor is an electromechanical or electrical device.

7. The system according to claim 1, wherein the first and second sensors are a hydraulic sensor and the first and second transducers are a hydraulic signal transducer, the first and second sensor conduits and the first and second transducer conduits are hydraulic conduits.

8. The system according to claim 1, wherein the tactile display is adapted to be arranged in a casing of the body extremity prosthesis.

9. The system according to claim 1, wherein the support is made of a flexible material and is adapted to be attachable to and detachable from a body extremity.

10. The system according to claim 1, wherein said prosthesis is a prosthesis for an arm or leg or part thereof.

11. The system according to claim 10, wherein said prosthesis is a forearm, hand or finger prosthesis.

12. The system according to claim 10, wherein said prosthesis is a lower leg, foot or toe prosthesis.

13. The system according to claim 1, further comprising a glove in which the first and second sensors are positioned, wherein said glove is adapted to be used on a hand, arm or finger without sensation or partially without sensation.

14. The system according to claim 1, further comprising a sock in which the first and second sensors are positioned, wherein said sock is adapted to be used on a foot, leg or toe without sensation or partially without sensation.

* * * * *